United States Patent [19]

Zaiger et al.

[11] Patent Number: Plant 5,813

[45] Date of Patent: Dec. 2, 1986

[54] PLUM TREE (BLUE KNIGHT)

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 671,334

[22] Filed: Nov. 13, 1984

[51] Int. Cl.[4] ..... A01H 5/03

[52] U.S. Cl. ..... Plt./38

[58] Field of Search ..... Plt./38

*Primary Examiner*—Robert E. Bagwill

[57] ABSTRACT

A new variety of plum tree which has the following unique combination of features which are outstanding in a new variety:

1. Heavy and regular bearing of uniform fruit throughout the tree.
2. Fruit coloring 2 weeks before maturity.
3. The extreme firmness of fruit and its good shipping characteristics.
4. Uniform coloring of the skin giving the fruit a very attractive appearance.

1 Drawing Figure

ORIGIN OF THE VARIETY

The herein variety of plum tree was originated by us in the experimental orchard located at Modesto, Stanislaus County, Calif., as follows: Seedlings were grown from seeds of an open pollinated Red Beaut Plum Tree (U.S. Plant Pat. No. 2,539) and a seedling was selected and labeled 4W52. A large number of open pollinated seeds from the plum selection 4W52 were grown under careful observation by us, one such seedling which is the present variety, having been especially desirable with respect to the fruit, was selected for asexual reproduction and commercialization.

ASEXUAL REPRODUCTION OF THE VARIETY

The present variety of plum tree was asexually reproduced by budding, as performed at Modesto, Calif., shows that said characteristics come true to form and are transmitted through succeeding propagations.

SUMMARY OF THE VARIETY

The present variety relates to a new and distinct variety of plum tree which is of large size, vigorous, upright in growth and a regular and productive bearer of medium size, very firm, yellow flesh clingstone fruit. The tree is further characterized by having fruit that colors 2 weeks before maturity, with an attractive blackish blue skin color and when compared to Red Beaut Plum (U.S. Plant Pat. No. 2,539) the fruit is larger in size, matures 10 days later, and the tree is more productive and a regular bearer of fruit.

BRIEF DESCRIPTION OF THE PHOTOGRAPH

The accompanying photographic illustrations show typical specimens of the foliage and fruit of the new variety, an exterior and sectional view of the fruit with the stone in place, and a small branch with the upper and lower surface of the foliage being illustrated.

DESCRIPTION OF THE VARIETY

The following is a detailed botanical description of the new and distinct variety of plum tree, its foliage and fruit, with color terminology (except those in common color terms) in accordance with Reinhold Color Atlas by Kornerup and J. H. Wanscher are based upon observations of specimens grown at Modesto, Calif.

Tree:
- *Size.*—Large.
- *Vigor.*—Vigorous.
- *Dense.*—Medium dense.
- *Shape.*—Upright. Normally pruned to vase form.
- *Production.*—Productive.
- *Bearer.*—Regular.

Trunk:
- *Size.*—Medium to stocky.
- *Texture.*—Shaggy.

Branches:
- *Size.*—Medium stocky.
- *Texture.*—Medium rough. Medium shaggy.
- *Color.*—Brown to reddish brown.
- *Lenticels.*—Numerous. Medium size.

Leaves:
- *Size.*—Medium. Average length — $4\frac{1}{4}''$. Average width — $1\frac{3}{4}''$.
- *Texture.*—Smooth.
- *Petiole.*—Medium. Average length — $\frac{3}{4}''$.
- *Shape.*—Lanceolate.
- *Margin.*—Serrate.
- *Glands.*—Reniform. Number varies: 2 to 3. Average number: 2.
- *Color.*—Upper surface — dark green (28-F-7) to (28-F-8). Upper surface — grayish green (28-D-8) to (28-E-7).

Flower buds:
- *Size.*—Medium.
- *Form.*—Plump, free.
- *Length.*—Medium.

Flowers:
- *Size.*—Medium.
- *Blooming period.*—Date of First Bloom Feb. 26, 1983. Date of Full Bloom Mar. 3, 1983.
- *Color.*—White.

Fruit:
- *Maturity when described.*—Firm ripe.
- *Date of first picking.*—June 13, 1983.
- *Date of last picking.*—June 19, 1983.
- *Size.*—Medium. Average diameter axially — $2\frac{3}{16}''$. Average transversely in suture plane — $2\frac{1}{8}''$. At right angles to suture plane — $2\frac{1}{8}''$.
- *Form.*—Globose. Nearly symmetrical.
- *Suture.*—Shallow.

*Ventral surface.*—Rounded.

*Cavity.*—Rounded. Average depth — ⅜". Average breadth — ½".

*Apex.*—Usually rounded. Varied from retuse to very slight pistol point.

Skin:

*Thickness.*—Medium.

*Texture.*—Medium. Tenacious to flesh.

*Tendency to crack.*—None.

*Down.*—Wanting.

*Color.*—Dark violet (18-F-8) to blackish blue (19-F-8).

Flesh:

*Color.*—Grayish yellow (4-B-7) to (5-B-6).

*Surface of pit cavity.*—Brownish orange (4-C-5) to yellowish brown (5-D-5).

*Texture.*—Firm, meaty.

*Ripens.*—Evenly.

*Flavor.*—Mild, subacid.

*Aroma.*—Very little.

*Eating quality.*—Good.

Stone:

*Type.*—Clingstone.

*Form.*—Ovid.

*Size.*—Medium. Average Length — 1". Average width — 9/16". Average thickness — 5/16".

*Base.*—Straight.

*Apex.*—Acuminate.

*Sides.*—Equal.

*Surface.*—Irregularly furrowed and ridged near base.

*Tendency to split.*—None.

*Color.*—From brownish orange (7-C-6) to light brown (7-D-6).

Use:

*Market.*—Local and long distance.

Keeping quality: Very good.

Shipping quality: Good.

The plum tree and its fruit herein described may vary in slight detail due to climatic and soil conditions under which the variety may be grown; the present description being of the variety as grown in the experimental orchard at Modesto, Calif.

The following is claimed:

1. A new and distinct variety of plum tree, as illustrated and described, characterized by its vigorous, upright growth and a heavy regular bearer of medium size, very firm, yellow flesh fruit with an attractive blackish blue skin color; characterized in comparison to Red Beaut, (U.S. Plant Pat. No. 2,539); by having fruit that matures 10 days later, is larger in size, colors 2 weeks before maturity and the tree is more productive and a regular bearer of fruit.

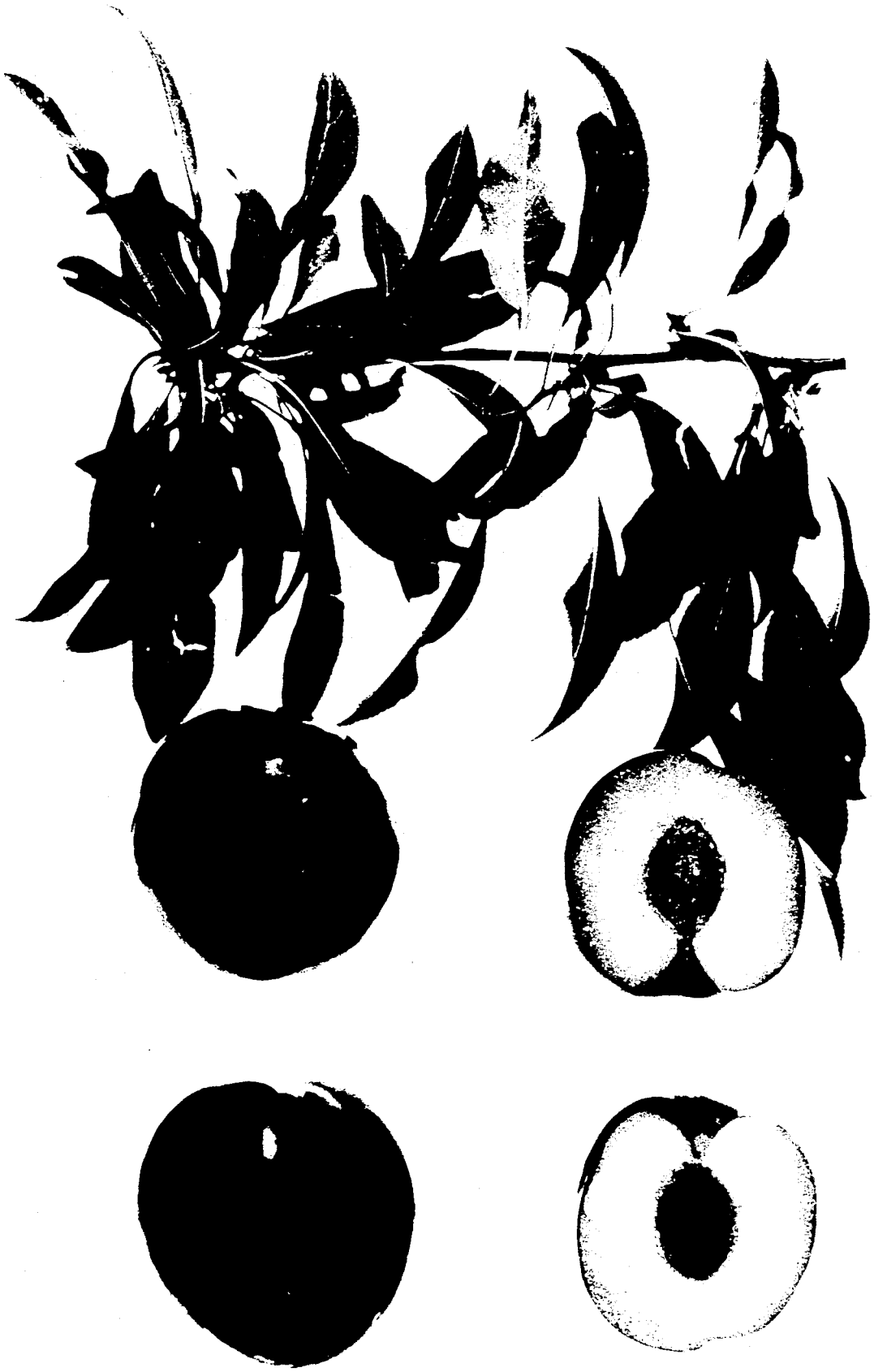

* * * * *